(12) United States Patent
Bernsteiner

(10) Patent No.: US 8,777,948 B2
(45) Date of Patent: Jul. 15, 2014

(54) DEVICE FOR SHORTENING AN ELONGATED BONE

(75) Inventor: René Bernsteiner, Graz (AT)

(73) Assignee: I.T.S. GmbH, Lassnitzhoehe (AT)

( * ) Notice: Subject to any disclaimer, the term of this patent is extended or adjusted under 35 U.S.C. 154(b) by 416 days.

(21) Appl. No.: 13/131,473

(22) PCT Filed: Oct. 19, 2009

(86) PCT No.: PCT/AT2009/000405
§ 371 (c)(1),
(2), (4) Date: May 26, 2011

(87) PCT Pub. No.: WO2010/060124
PCT Pub. Date: Jun. 3, 2010

(65) Prior Publication Data
US 2011/0238068 A1    Sep. 29, 2011

(30) Foreign Application Priority Data
Nov. 27, 2008 (AT) ............................... A 1851/2008

(51) Int. Cl.
*A61B 17/80* (2006.01)
(52) U.S. Cl.
USPC ........................................................ 606/70
(58) Field of Classification Search
USPC ...................... 606/70, 71, 86 R, 90, 280–299
See application file for complete search history.

(56) References Cited

U.S. PATENT DOCUMENTS

| 4,929,247 A | 5/1990 | Rayhack |
| 5,042,983 A | 8/1991 | Rayhack |
| 2005/0277941 A1 | 12/2005 | Trumble et al. |
| 2007/0270850 A1* | 11/2007 | Geissler .......................... 606/69 |
| 2007/0276383 A1* | 11/2007 | Rayhack ......................... 606/69 |

FOREIGN PATENT DOCUMENTS

| WO | 2007/067829 | 11/2007 |
| WO | 2007/127994 | 11/2007 |

* cited by examiner

*Primary Examiner* — Christopher Beccia
(74) *Attorney, Agent, or Firm* — Greenblum & Bernstein, P.L.C.

(57) ABSTRACT

The invention relates to a device (1) for shortening an elongated bone, in particular an ulna, comprising a bone plate (5) to be attached to the bone with a hole (6) for a fastening element for fixing the bone plate (5) on the bone and a slot offset longitudinally thereto for a holding element (9) that can be fastened in the bone, so that after the bone has been severed and a piece of bone has been removed in the region between the hole (6) and the slot, bone parts can be guided together by the displacement of the bone plate relative to the holding element (9). In order to create a device (1), which is constructed with a small space requirement and permits a highly accurate guiding together of the bone parts, it is provided according to the invention that a block (12) with an opening (13) for the holding element (9), which opening is elongated in plan view and lies above the slot, is arranged on the bone plate (5) in the region of the slot, wherein a unit (14) is arranged in the opening (13), against which unit the holding element (9) rests in the displacement direction and relative to which a remaining part of the block (12) can be displaced with the aid of a provided adjustment element (15).

17 Claims, 4 Drawing Sheets

DEVICE FOR SHORTENING AN ELONGATED BONE

Figure 1:
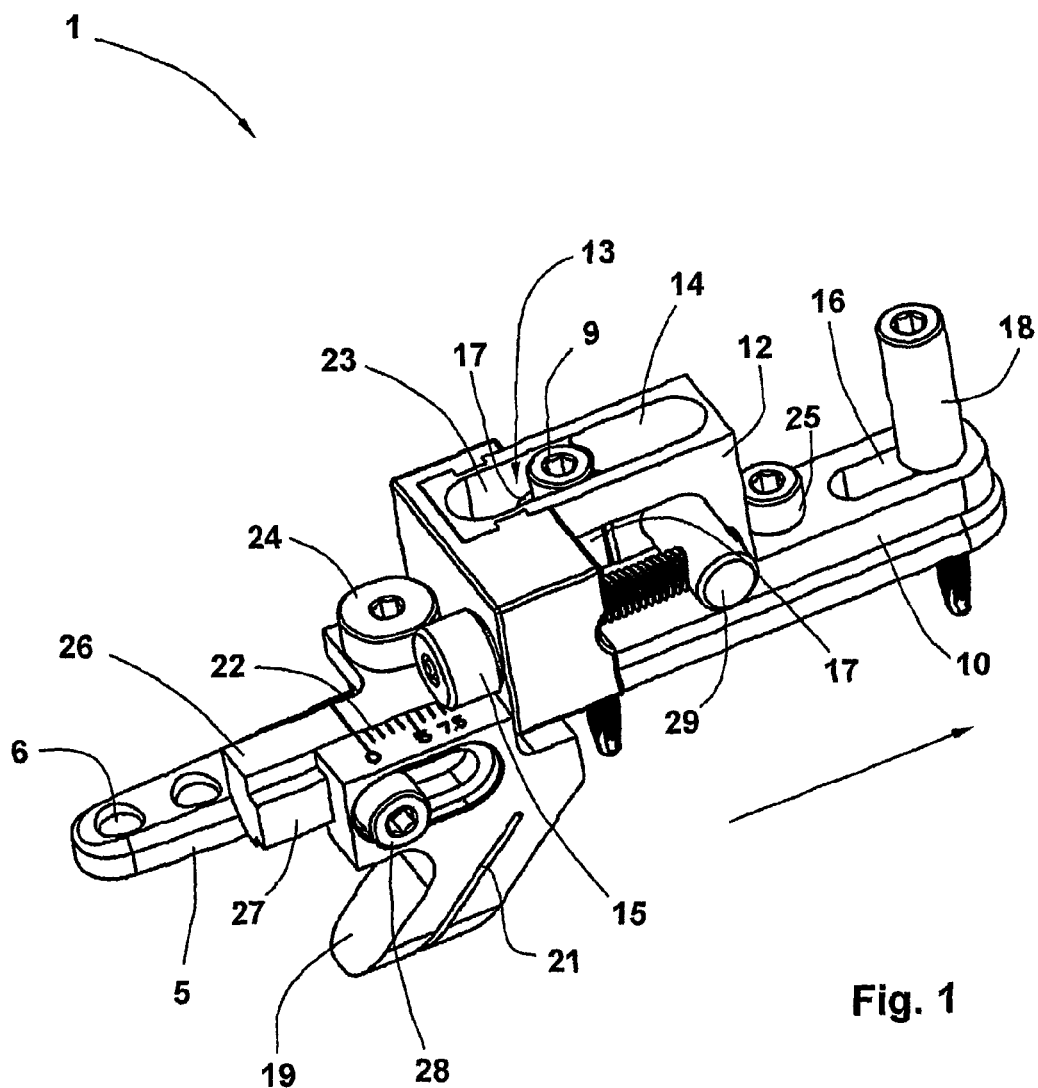

The invention relates to a device for shortening an elongated bone, in particular an ulna, comprising a bone plate to be attached to the bone with a hole for a fastening element for fixing the bone plate on the bone and a slot offset longitudinally thereto for a holding element that can be fastened in the bone, so that after the bone has been severed and a piece of bone has been removed in the region between the hole and the slot, bone parts can be guided together by the displacement of the bone plate relative to the holding element.

A limited freedom of movement of a person's wrist can be caused by an excessive curvature of an ulna. One way of correcting this and thereby increasing the freedom of movement of the wrist, is to shorten the ulna. The procedure in this case is to sever the ulna at two points along parallel planes, after severing, a piece of bone of the ulna is removed and thereafter the bone parts are guided together in the region of the parallel planes. Subsequently, the bone parts grow together in the region of the planes guided together, so that after the bone parts have grown together, the ulna is shortened and less markedly curved.

A shortening of an ulna must be carried out with high precision so that only the curvature thereof is corrected, but defective positions are not caused by the procedure performed, e.g., a twisted position of the temporarily severed bone parts due to twisting of the bone parts while being guided together and while the said bone parts are subsequently growing together.

According to the prior art, various devices have already been proposed for shortening an ulna. From printed publication US 2005/0277941 A1 a bone plate is known, which remains fastened to the bone after the ulna has been shortened and is equipped with additional devices, which during a removal of a piece of bone interact with the bone plate and are used to hold separated bone parts which are present after the removal of a piece of bone, and to guide them together. These devices comprise a guide device for a saw for producing parallel cuts in the bone or for severing the same. Furthermore, holding elements are provided in the form of nails, which are placed in slots of the bone plate and are fastened in the bone. The bone plate is fastened to the bone in at least one further position with a screw in a shear-resistant manner. After the bone has been severed and a piece of bone has been removed, a forceps is placed on the bone plate in the fastened region, and the separated bone parts are guided together, wherein the forceps can engage in a further position on the provided nails, which serve as a holder, so that the bone plate is moved with one bone part relative to the nails located in the provided slots and the other bone part. Although a device of this type allows bone parts to be guided together, it is disadvantageous that a shortening of an ulna with this device can hardly be carried out by a single person or cannot be carried out by a single person at all. Namely, the bone plate still needs to be fixed on one bone part after the bone parts have been guided together. However, at the same time it is necessary to keep the bone parts in contact with the forceps, which is why the handling during a shortening of an ulna or an operation is difficult. Furthermore, manual guiding together with the aid of the forceps is a potential source of errors, since there is no exact control of the guiding together of the bone parts.

A device is known from printed publication U.S. Pat. No. 4,929,247, which likewise can be used in the shortening of an ulna. This device comprises a bone plate with several holes for fastening the bone plate to the bone as well as a slot. In addition, the device comprises two blocks, which are attached to the bone on both sides of a piece of bone to be removed with long retaining pins, wherein a retaining pin is guided through the slot. Finally, the two blocks arranged projecting upwards on the bone plate in a perpendicular manner are connected with two screws running parallel to the bone plate or horizontally, through which the blocks can be moved relative to one another. If a piece of bone has been removed in the region between the blocks, the adjustment screws are actuated and the bone parts are thereby moved towards one another. Thereafter the bone plate is fixed to the bone and the blocks are removed from the bone plate by releasing the retaining pins. However, it is a disadvantage with this device that it requires a large amount of space due to the two blocks that are necessary, which can lead to disadvantages in handling the device during an operation, since in an operation only a small incision is generally desirable, and therefore available space is small.

From U.S. Pat. No. 5,042,983 a cutting device is known for removing a piece of bone of an ulna. This device is used in conjunction with a device according to previously cited document U.S. Pat. No. 4,929,247. The cutting device is positioned on a supporting plate, which corresponds to the bone plate according to document U.S. Pat. No. 4,929,247. In a first step, the cutting device is fastened to the bone in predetermined positions with the corresponding supporting plate. After the bone has been severed and a piece of bone has been removed, the cutting device or the supporting plate is removed and the bone plate according to document U.S. Pat. No. 4,929,247 is placed in order to guide the bone parts together. However, it is disadvantageous in this approach that, in addition to the disadvantages mentioned above, the bone plate has to be fastened with positional accuracy in those holes in which the supporting plate of the cutting device was also previously positioned, which is associated with an uncertainty with regard to the position of bone parts present separated from one another during the guiding together of the same.

A removal of a piece of bone of an ulna and a subsequent arrangement of a device together with a bone plate and a guiding together of bone parts in two separate steps or with two separate devices is also known from document US 2007/0276383 A1.

The object of the invention is to disclose a device of the type mentioned at the outset which is constructed with a small space requirement and permits a highly accurate guiding together of the bone parts.

This object is attained with a device of the type mentioned at the outset when a block with an opening for the holding element, which opening is elongated in plan view and lies above the slot, is arranged on the bone plate in the region of the slot, wherein a unit is arranged in the opening, against which unit the holding element rests in the displacement direction and relative to which a remaining part of the block can be displaced with the aid of a provided adjustment element.

In a device according to the invention it is advantageous that it has only one block, which interacts with a holding element, so that a compact construction is given. During the use of the device, the holding element, seen in the displacement direction of the bone plate, bears against the unit positioned in the opening, so that the unit cannot move against the displacement direction. Therefore only a movement of the remaining part of the block in the displacement direction is possible, which can be performed with the provided adjustment element. Furthermore, a highly accurate guiding together of bone parts after the removal of a piece of bone is possible, since the block is already arranged on the bone plate and a shear-resistant attachment of the bone plate can also be carried out on the second bone part directly after the bone parts have been guided together. After the attachment of the bone plate, the block can then be removed.

The device according to the invention can be used in principle for shortening any bones in humans or in animals. However, the device according to the invention is preferably used in the shortening of an ulna. For this purpose the bone plate is embodied in an elongated manner corresponding to a sectional course of the ulna.

The provided block can be arranged directly on the bone plate. However, it is particularly preferred for the block to be embodied with extensions on the base which define a further plate, which is embodied at least in part with approximately the same width as the bone plate, but shorter. A region for fastening the block to the bone plate is created by the provided extensions, which, as mentioned, are located on the base. Since the extensions are arranged on the base and are embodied to be flat, no disadvantage results thereby with respect to space requirements. The block is thereby expediently arranged approximately centrally on the bone plate, which requires the slot of the bone plate to also be arranged approximately centrally on the same. This provides the advantage that the block, which requires the largest space requirement during an operation, lies approximately in the center of a cut, e.g., along a forearm, where the skin can be spread furthest and thus most space is available for attaching the device. In principle the block can also be arranged approximately at the end of the bone plate, although in this case an operation is somewhat more difficult, since the block then has to be fastened on the bone in the region of an end of an incision together with the bone plate. In any case it is expedient for the bone plate and the further plate to respectively have a slot, which slots are arranged one above the other and are located at an end of the bone plate lying opposite the hole. Then two holding elements can be used, wherein one holding element is in engagement with the block and the further holding element serves to guide the bone plate in a straight line while guiding the bone parts together.

In order for it to be possible to move the bone plate as far as possible without even the slightest twisting of one of the bone parts relative to one another, a device according to the invention is expediently embodied such that the holding element and a further holding element are provided, which engage in the slot and the opening of the block or the slots and are formed in an elongated manner with a cylindrical part and a part having a thread, wherein the cylindrical part in the block bears against the unit or against the further plate. In this respect it has proven to be expedient for the slots of the bone plate and a free region of the opening into which the holding element is guided or the slot of the further plate to be embodied with approximately the same dimensions.

The further plate is generally attached to the bone plate in a detachable manner, so that the further plate together with the block can be separated from the bone plate, as soon as the bone parts bear against one another and are respectively fixed by the bone plate.

It is particularly expedient for a guide device for a cutting device to be detachably fastened to the further plate, e.g., at the side of the guide device. This makes it possible to sever a bone as precisely as possible. In order to be able to place cuts along a bone in a variable manner, it can be provided thereby that the guide device can be fixed in a variable manner relative to the further plate. It is then sufficient for the guide device to have only one guide slot. If in addition a scale is provided, on which a position of the guide device relative to the further plate can be read off, a piece of bone can be removed with a desired or predetermined length. This has hitherto not been possible or possible only in individual cases according to the prior art, since only guide devices with several parallel guide slots with predetermined constant spacing were provided. This permitted only a removal of pieces of bone which corresponded to a whole-number multiple of the spacing between two guide slots.

The guide device is preferably detachably fastened to the further plate, so that the guide device can be removed after the severing of the bone but still before the guiding together of the bone parts and thus is not in the way while the bone parts are guided together.

In order to make it possible to guide the bone parts together with great precision or to control a contact pressure of the bone parts before fixing the bone plate, the remaining part of the block is advantageously continuously displaceable by the adjustment element.

Likewise with respect to an exact guiding together of the bone parts, it can be provided for the unit to partially surround the holding element. A position change of the holding element relative to the unit is prevented or at least largely ruled out by this measure.

The adjustment element can be embodied as an adjustment screw, which is arranged in or on the remaining part of the block, and is connected to the unit. It is expedient thereby for the adjustment screw to run approximately parallel to the bone plate in the displacement direction.

It is furthermore advantageous that the unit can be placed into the opening and the block has lateral recesses running in the displacement direction, through which a holding means connected to the adjustment element and holding the unit vertically in position is guided. This contributes to a smooth displacement of the remaining part of the block relative to the unit, since the holding means in interaction with the recesses serves to guide the remaining part of the block.

Figure 3:
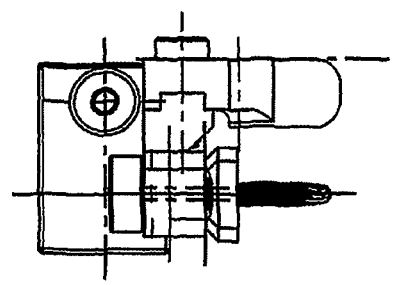
Figure 2:
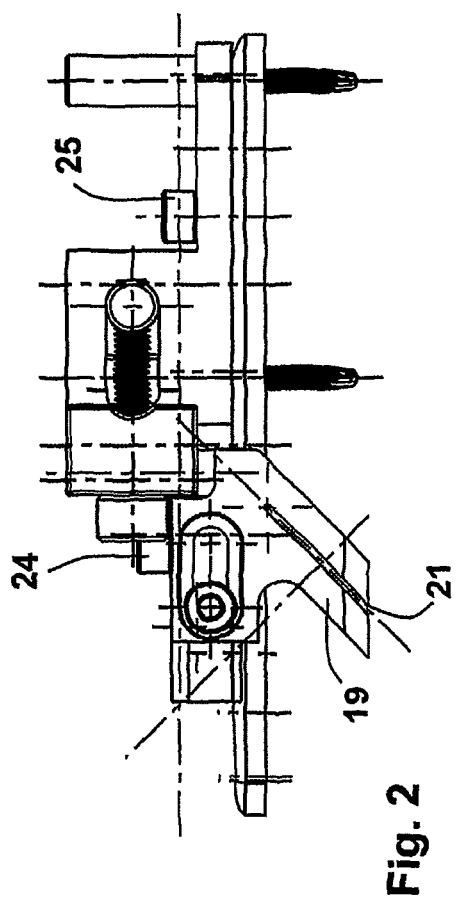
Figure 4:
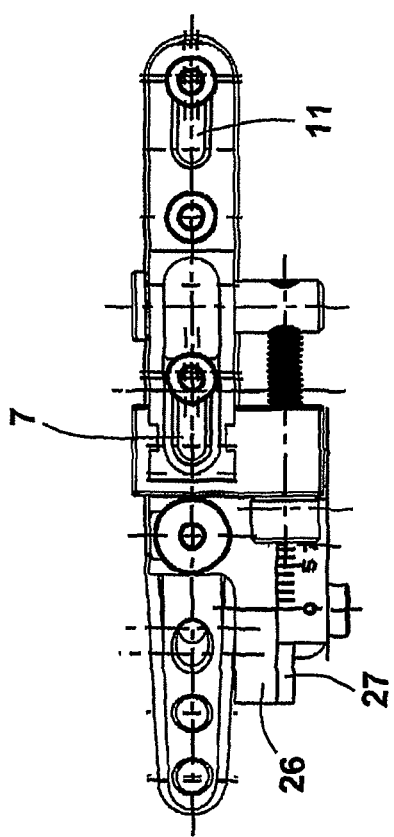
Figure 5:
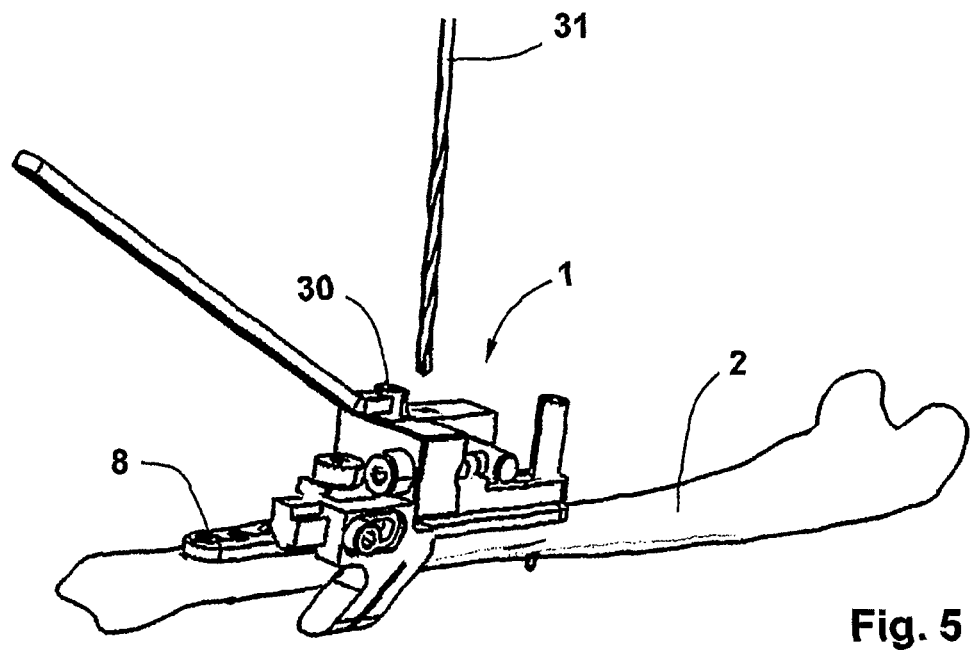
Figure 6:
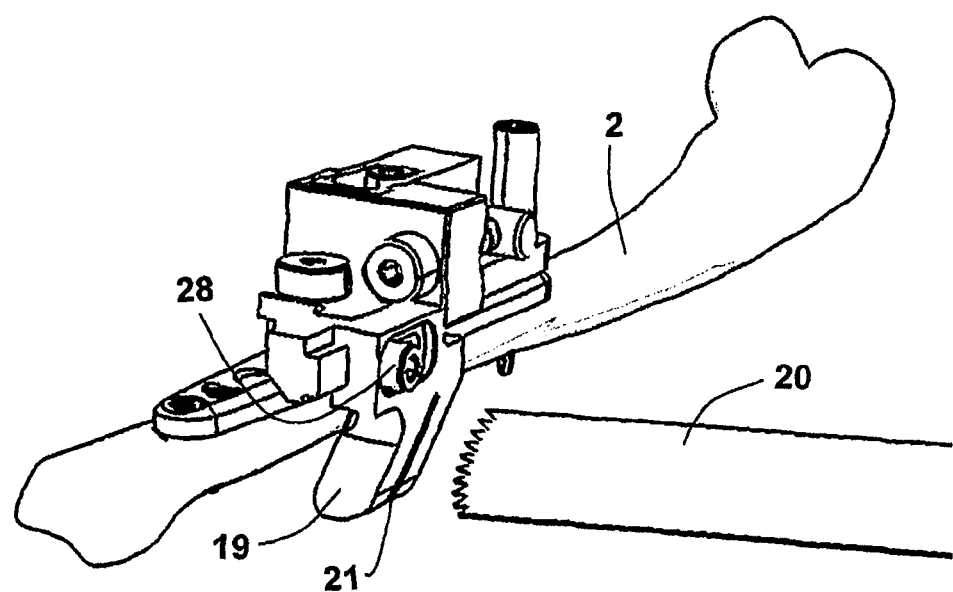
Figure 7:
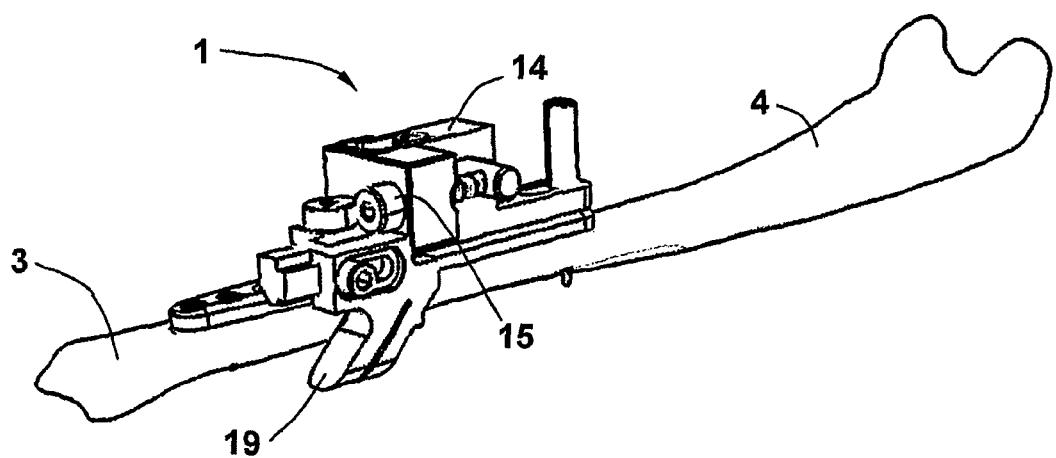
Figure 8:
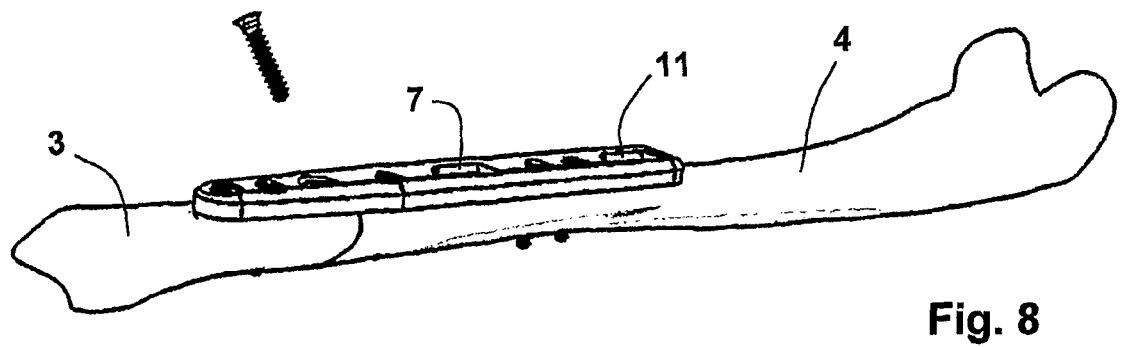

Further features, advantages and effects of the invention are shown by the exemplary embodiment shown below and the drawings. The drawings show:

FIG. 1 A device according to the invention in perspective representation;

FIG. 2 A device according to the invention in a side view;

FIG. 3 The device shown in FIG. 2 in front view;

FIG. 4 The device shown in FIG. 2 in plan view;

FIG. 5 A diagrammatic representation of the arrangement of a device according to the invention on a bone;

FIG. 6 A diagrammatic representation of the severing of a bone;

FIG. 7 A diagrammatic representation similar to FIG. 6 after the removal of a piece of bone;

FIG. 8 A bone with an attached bone plate.

FIGS. 1 through 4 show a device 1 according to the invention in various views. The device 1 comprises a bone plate 5, which has a hole 6 on the end, which hole is embodied to be approximately round in plan view. In addition, the bone plate 5 has a slot 7 as well as a further slot 11, the positions or situations of which are explained later. The bone plate 5 is embodied in an elongated manner and is generally composed of a metal such as titanium.

A block 12 is arranged on the bone plate 5. The block 12 is embodied on the base with two extensions extending along the bone plate 5, which jointly define a further plate 10. The further plate 10 and the extensions of the block 12 respectively are detachably fastened to the bone plate 5 with fastening means 24, 25, e.g., screws. On an end of the bone plate 5 opposite the hole 6 of the same arranged on the end, the further plate 10 and the corresponding extension of the block 12 respectively extend approximately to the end of the bone plate 5 and in this end region has a slot 16. This slot 16 is positioned above the further slot 11 of the bone plate 5 embodied with corresponding dimensions. The slot 11 in FIGS. 1 through 4 is partially covered by the further plate 10 and can be clearly seen only after the further plate 10 has been removed. In this region the further plate 10 is embodied with a width, which corresponds approximately to that of the bone plate 5.

The other part of the further plate 10 and the extension of the block 12, which extends from the block 12 to the end hole 6 of the bone plate 5, is embodied in a region adjoining the block 12 such that the further plate 10 in the region of the fastening means 24 on one side is approximately flush with the bone plate 5, but on the other side has a tongue 26 projecting in the direction of the hole 6 of the bone plate 5, which can be seen in particular from FIGS. 2 through 4. The tongue 26 has on the outside a rail 27 running approximately parallel to the bone plate 5. A guide device 19 is arranged on the rail 27. The guide device 19 has a guide slot 21, through which, for example, a saw can be guided, so that during a severing of an ulna the saw does not leave the plane defined by the guide slot 21. An upper part of the guide device 19 surrounds the rail 27. For this purpose, the guide device 19 is embodied with a groove corresponding to a profile of the rail 27. In the upper part of the guide device 19 furthermore a scale 22 is located, based on which a position of the guide device 19 relative to the further plate 10, with respect to which the guide device 19 can be displaced, can be read off. To this end, a marking is provided on the further plate 10. The displaceability of the guide device 19 is achieved in that the guide device 19 has a lateral opening running horizontally in which a holding element 28 engaging in the rail 27 is arranged, which holding element can be released so that the guide device 19 can be displaced along the opening depending on requirements or the length of a piece of bone to be removed. Based on the scale 22 provided, a length of the piece of bone to be removed can be precisely adjusted. The advantage is thereby given at the same time that for two cuts to be made, respectively the same guide slot 21 is used as guide means, which means that two essentially parallel cutting planes are obtained, which has proven to be favorable after the removal of a piece of bone and the guiding together of parts of an ulna or while the parts are growing together. As can be seen from FIG. 2, for example, the guide slot 21 is arranged in a lower part of the guide device 19 and runs approximately at an angle of 45° to the bone plate 5.

The block 12 is arranged approximately centrally on the bone plate 5. As mentioned, the block 12 is embodied with extensions on the base, which define a further plate 10. This is an advantage with regard to easy handling of the device 1. However, it is also possible for the block 12 and the further plate 10 to be embodied separately. In this case, the block 12 bears on the further plate 10. The block 12 has a central opening 13. A length of this opening 13 is dimensioned such that it covers at least the slot 7 of the bone plate 5 arranged beneath it. A holding element 9 can thereby be positioned in the opening 13 of the block 12. A further holding element 18 is positioned in the insert in the slots 7, 11 of the bone plate 5 or the further plate 10.

As can be seen from FIGS. 1 through 4, a unit 14 is arranged in the opening 13 of the block 12. This unit 14 essentially completely fills a region of the opening 13 lying between the holding element 9 embodied as a tensile bolt and an end of the opening 13. The unit 14 is embodied in a semicircular manner in the region of the holding element 9 and thus surrounds the holding element 9 or the tensile bolt. The unit 14 is detachably fixed with a holding means 29. The holding means 29 or the retaining pin penetrates the block 12 and according to the representation in FIG. 1 projects through lateral recesses 17 of the block 12 perpendicular to the bone plate 5. An adjustment element 15, namely an adjustment screw engages in the laterally projecting part of the holding means 29. The adjustment element 15 embodied as an adjustment screw penetrates the block 12 parallel to the displacement direction or the bone plate 5 and lies at the level of the retaining means 29. If the device 1 in the form shown in FIG. 1 is attached to an ulna and a piece of bone has already been removed, two parts of the ulna separated and spaced apart from one another can be moved with respect to one another by rotating the adjustment screw until they bear against one another. Since the unit 14 does not move with the rotating adjustment screw, the remaining part of the block 12 with the attached bone plate 5 must move in the displacement direction shown by an arrow in FIG. 1, wherein the holding element 9 runs through a free region 23 of the opening 13 at least in part. The remaining part of the block 12 thereby runs via the holding means 29.

Based on FIGS. 5 through 8, the use of the device 1 according to FIGS. 1 through 4 is shown diagrammatically during an operation or a shortening of an ulna. The device 1 is placed on a bone 2 like an ulna, after the bone 2 has been exposed for the operation. After the placement of the device 1, this is fixed at the end on the bone 2 at a hole 6 with a fastening element 8, such as a screw. Furthermore, holding elements 9, 18, having a thread on the foot are arranged in the opening 13 of the block 12 or in the slot 7 of the bone plate 5 and the end slots 11, 16 and fastened in the bone 2. For this purpose, as can be seen from FIG. 5, a well-fitting adapter 30 is inserted into the free region 23 of the opening 13. This adapter 30 is embodied in a precisely fitting manner for the free region 23 and the slots 7, 11, 16 respectively, and has an opening running vertically, through which a drill 31 can be guided. Based on an embodiment with identical dimensions of the free region 23 and the slots 7, 11, 16, the adapter 30 can be used multiple times and thus is used for drilling a hole in the bone 2 for the holding element 9 as well as as a guide and positioning aid for the holding element 18.

If the device 1 is fastened to the bone 2, a first severing of the bone 2 can be carried out with a suitable cutting device 20 (FIG. 6). After a first severing of the bone 2 has been carried out, the holding element 28 is released and the guide device 19 is displaced on the rail 27 corresponding to a length of a piece of bone to be removed and subsequently fixed again with the holding element 28 before a second cut is made. Following the second cut, the piece of bone of predetermined length is removed. Now a situation such as that shown in FIG. 7 has been attained, wherein bone pieces 3, 4, are still spaced apart from one another. The gap produced by the removal of the piece of bone is covered by the guide device 19 of the device 1 in FIG. 7. With the aid of the adjustment screw or the adjustment element 15, the bone part 3 is now moved to the bone part 4 in the manner described above. As soon as the bone part 3 bears against the bone part 4, the bone plate 5 can also be fixed on the bone part 4. When the bone plate 5 has been fixed with screws to both of the bone parts 3, 4, the device 1 can be removed. Then a situation shown in FIG. 8 is reached. If needed, a further screw can be driven into the bone, namely obliquely in the region of the connection surfaces of the bone parts 3, 4, so that the bone parts 3, 4 are additionally held pressed against one another.

The invention claimed is:
1. Device for shortening an elongated bone, comprising a bone plate to be attached to the bone with a hole for a fastening element for fixing the bone plate on the bone and a slot offset longitudinally from the hole for a holding element that can be fastened in the bone, so that after the bone has been severed to form bone parts and a piece of bone has been removed in the region between the hole and the slot, remaining bone parts can be guided together by the displacement of the bone plate relative to the holding element, wherein a block with an opening for the holding element, which opening is elongated in plan view and lies above the slot, is arranged on the bone plate in the region of the slot, wherein a unit is arranged in the opening, against which unit the holding element rests in the displacement direction and relative to which a remaining part of the block can be displaced with the aid of a provided adjustment element.

2. Device according to claim 1, wherein the bone plate is embodied in an elongated manner.

3. Device according to claim 1, wherein the block is embodied with extensions on the base which define a further plate, which is embodied at least in part with approximately the same width as the bone plate, but shorter.

4. Device according to claim 3, wherein the bone plate and the further plate respectively have a slot, which slots are arranged one above the other and are located at an end of the bone plate lying opposite the hole.

5. Device for shortening an elongated bone, comprising a bone plate to be attached to the bone with a hole for a fastening element for fixing the bone plate on the bone and a slot offset longitudinally from the hole for a holding element that can be fastened in the bone, so that after the bone has been severed to form bone parts, and a piece of bone has been removed in the region between the hole and the slot, remaining bone parts can be guided together by the displacement of the bone plate relative to the holding element, wherein a block with an opening for the holding element, which opening is elongated in plan view and lies above the slot, is arranged on the bone plate in the region of the slot, wherein a unit is arranged in the opening, against which unit the holding element rests in the displacement direction and relative to which a remaining part of the block can be displaced with the aid of a provided adjustment element, wherein the block is embodied with extensions on the base which define a further plate, which is embodied at least in part with approximately the same width as the bone plate, but shorter, wherein the bone plate and the further plate respectively have a slot, which slots are arranged one above the other and are located at an end of the bone plate lying opposite the hole, and wherein the holding element and a further holding element are provided, which engage in the slot and the opening of the block or the slots and are formed in an elongated manner with a cylindrical part and a part having a thread, wherein the cylindrical part in the block bears against the unit or against the further plate.

6. Device according to claim 3, wherein the further plate is attached to the bone plate in a detachable manner.

7. Device according to claim 3, wherein a guide device for a cutting device is detachably fastened to the further plate.

8. Device according to claim 7, wherein the guide device can be fixed in a variable manner relative to the further plate.

9. Device according to claim 7, wherein the guide device has a guide slot and a scale, on which a position of the guide device relative to the further plate can be read off.

10. Device according to claim 6, wherein the guide device is detachably fastened to the further plate.

11. Device according to claim 1, wherein the remaining part of the block can be displaced continuously by the adjustment element.

12. Device according to claim 1, wherein the unit partially surrounds the holding element.

13. Device according to claim 1, wherein the adjustment element is embodied as an adjustment screw, which is arranged in or on the remaining part of the block, and is connected to the unit.

14. Device according to claim 13, wherein the adjustment screw runs approximately parallel to the bone plate in the displacement direction.

15. Device according to claim 1, wherein the unit can be placed into the opening and the block has lateral recesses running in the displacement direction, through which a holder connected to the adjustment element and holding the unit vertically in position is guided.

16. Device according to claim 5, wherein the slots of the bone plate and a free region of the opening into which the holding element is guided or the slot of the further plate are embodied with approximately the same dimensions.

17. Device for shortening the elongated bone according to claim 1, wherein the elongated bone is an ulna.

* * * * *